(12) United States Patent
Katz

(10) Patent No.: US 6,488,617 B1
(45) Date of Patent: Dec. 3, 2002

(54) METHOD AND DEVICE FOR PRODUCING A DESIRED BRAIN STATE

(75) Inventor: Bruce F. Katz, Haverford, PA (US)

(73) Assignee: Universal Hedonics, Haverford, PA (US)

( * ) Notice: Subject to any disclaimer, the term of this patent is extended or adjusted under 35 U.S.C. 154(b) by 6 days.

(21) Appl. No.: 09/687,599

(22) Filed: Oct. 13, 2000

(51) Int. Cl.⁷ .......................... A61M 21/00; A61B 5/04
(52) U.S. Cl. ........................................ 600/26; 600/544
(58) Field of Search ............................ 600/9–15, 300, 600/544, 545, 26–27, 409; 128/897; 607/45

(56) References Cited

U.S. PATENT DOCUMENTS

| | | | |
|---|---|---|---|
| 3,882,850 A | | 5/1975 | Bailin et al. |
| 4,227,516 A | | 10/1980 | Meland et al. |
| 4,700,135 A | | 10/1987 | Hoenig |
| 4,736,751 A | * | 4/1988 | Gevins et al. ............ 600/545 |
| 4,940,453 A | | 7/1990 | Cadwell |
| 5,036,858 A | | 8/1991 | Carter et al. |
| 5,092,835 A | * | 3/1992 | Schurig et al. ............ 600/9 |
| 5,215,086 A | | 6/1993 | Terry, Jr. et al. |
| 5,280,793 A | | 1/1994 | Rosenfeld |
| 5,309,923 A | * | 5/1994 | Leuchter et al. ............ 600/544 |
| 5,356,368 A | | 10/1994 | Monroe |
| 5,495,853 A | | 3/1996 | Yasushi |
| 5,732,702 A | | 3/1998 | Mueller |
| 5,743,854 A | * | 4/1998 | Dobson et al. ............ 600/409 |
| 5,769,778 A | | 6/1998 | Abrams et al. |
| 5,813,993 A | * | 9/1998 | Kaplan et al. ............ 600/544 |
| 5,954,629 A | | 9/1999 | Yanagidaira et al. |
| 6,266,556 B1 | | 7/2001 | Ives et al. |
| 6,304,775 B1 | * | 10/2001 | Iasemidis et al. ............ 600/544 |

OTHER PUBLICATIONS

John R. Hughes, et al; "Conventional and Quantitative Electroencephalography in Psychiatry"; *The Journal of Neuropsychiatry and Clinical Neuroscience*, 1999; 11:2 190–208.

Daniel L. Menkes et al., "Right frontal lobe slow frequency repetitive transcranial magnetic stimulation (SF r–TMS) is an effective treatment for depression: a case–control pilot study of safety and efficacy;" *J. Neurol Neurosurgery Psychiatry* 1999; 67:113–115.

Andreas Killen; "Magnetic headbangers"; www.salon.com, Oct. 3, 2000.

* cited by examiner

Primary Examiner—Kevin Shaver
Assistant Examiner—Nikita R Veniaminov
(74) *Attorney, Agent, or Firm*—Wolf, Block, Schorr and Solis-Cohen LLP; Robert F. Zielinski; Eric A. Dichter

(57) ABSTRACT

A method and device for the production of a desired brain state in an individual contain means for monitoring and analyzing the brain state while a set of one or more magnets produce fields that alter this state. A computational system alters various parameters of the magnetic fields in order to close the gap between the actual and desired brain state. This feedback process operates continuously until the gap is minimized and/or removed.

30 Claims, 2 Drawing Sheets

METHOD AND DEVICE FOR PRODUCING A DESIRED BRAIN STATE

FIELD OF THE INVENTION

The present invention relates to monitoring and altering an individual's brain state. More particularly, the present invention is directed to the continuous real-time alteration of the brain state from a less desirable to a more desirable state through the use of multiple magnetic fields and a system monitoring the effect of the fields.

BACKGROUND OF THE INVENTION

Most techniques for altering the brain state of a subject have concentrated on altering a measure of this state, i.e., the electroencephalogram (EEG) signal. The EEG is an electrical signal that is read on the surface of the skull which reflects the average activity of large groups of neurons and may, if properly interpreted, be indicative of the psychological state of the subject. EEG frequency bands are usually divided into (1) delta rhythms, having a frequency range of 1.5–3.5 Hz, (2) theta rhythms, having a frequency range of 3.5–7.5 Hz, (3) alpha rhythms, having a frequency range of 7.5–12.5 Hz, and (4) beta rhythms, having a frequency range of 12.5–20 Hz. Some frequencies above 20 Hz, such as the gamma range (around 40 Hz) have been implicated in various types of cognitive processing, although their role in indicating overall mood is still unclear. In general, the lower the mean frequency of the EEG signal, the lower the state of alertness, although many other factors may influence the interpretation of the EEG signal, including the location on the scalp of the EEG readings, the degree of synchronization between readings, and whether any psychological pathology is present.

Conventional EEG monitoring techniques have involved a skilled technician processing the raw signals by hand. A well-trained technician can often pinpoint abnormalities in such signals, although well-defined correlates between EEG signals and pathological brain states have only been made possible with the advent of quantitative EEG (QEEG) methods, in which the analog EEG signal is converted to a digital signal for further computational manipulation and analysis. Among the many features that QEEG can easily detect are precise power levels in different bandwidths, dynamic changes in bandwidths over time, and coherence between different parts of the brain. In conjunction with some theoretical assumptions, QEEG may also be used to provide a three-dimensional picture of brain activity. QEEG has also revealed a number of correlates between abnormal electrical activity and pathological states, including but not limited to, the states of dementia, schizophrenia, mood disorders, Attention Deficit Disorders (ADD), and alcohol and substance abuse (Hughes & John, 1999). In addition, it has been known for some time that relatively high activity in the alpha frequency band (8–13 Hz) in normal subjects is correlated with a feeling of relaxation.

These sorts of results have encouraged researchers to attempt to improve deficient or otherwise non-optimal mental states by attempting to manipulate the EEG. For example, depression has been correlated with an asymmetry in activity between the right and left prefrontal cortices, with greater activity in the right. To treat this condition, one would want to achieve an EEG signal which is more balanced between the hemispheres. Likewise, one might attempt an increase in the power level of the alpha band to increase relaxation.

One method for altering the brain signals is by biofeedback (see, e.g., U.S. Pat. No. 3,882,850), in which a patient is given a visual or auditory feedback proportional to the desired EEG signal. The patient attempts to increase the level of this feedback in order produce more of the desired signal. For example, in alpha feedback, the intensity of a sound may represent the degree of alpha present. By concentrating on raising the intensity of this sound, the patient thereby indirectly increases the intensity of the degree of alpha present, and presumably thereby increases her degree of relaxation. U.S. Pat. No. 5,280,793 describes a similar feedback mechanism for the correction of hemispheric asymmetry in activity levels associated with depression.

There are, however, limitations on what can be accomplished with this treatment paradigm. First and most fundamentally, the method can only work if it is conceivable that conscious effort can alter the brain in the desired way. The exact neural dynamics of biofeedback are unknown, but it is known that conscious effort is localized to specific areas of the brain, most likely those of the neocortex. If the right connections to other areas of the brain that are in need of change are not present, or are of the wrong sort, then biofeedback will not be possible. In short, the situation is one of a part of a dynamic system attempting to influence the state of the dynamic system as a whole, which may work in certain cases, but is less likely to work when large-scale, and/or long-term change must be effected. Secondly, biofeedback may be providing duplicate information. For example, presumably one either knows or can be taught to pay attention to how relaxed one is. In this case, audible feedback of the EEG signal may be simply a more complex method of achieving what can be done with simpler means.

For these reasons and others, researchers have turned to other means of altering the underlying brain state, while maintaining the basic mechanism of EEG feedback. For example, U.S. Pat. No. 5,495,853 uses photic stimulation delivered to the eyes through specially constructed glasses in order to alter the brain state. Meanwhile, the EEG signal is monitored. If the desired EEG signal is not being produced, then certain parameters of the stimulation, such as the frequency of the flashing of the lights, are changed until the desired signal is achieved.

This method, however, suffers from a similar problem to that of biofeedback. Visual stimulation is routed primarily through the optic tract to the thalamus and then to the occipital cortex, where most primary visual processing is accomplished. It is only routed to other areas of the brain, if at all, after a number of filters have been applied to the visual signal, such as those responsible for line and shape extraction, those that divide the color information into three channels (red/green, blue/yellow, and black/white), and those that divide static from motion information. Thus, any attempt to influence a part of the brain other than the occipital cortex itself will be a hit and miss affair.

A method that has a more global effect on the brain is electro-convulsive therapy (ECT). ECT is achieved by applying a controlled current to the patient's skull for a period of 1–10 seconds, and is chiefly used in treatment of refractory depression. In recent years, ECT has been made much more safe than previously, although as U.S. Pat. No. 5,769,778, to Abrams et al. describes, it still suffers from a number of side effects, including burns to the scalp and skin and unwanted effects of the induced seizure, including memory loss. Furthermore, because the signal strength must be large enough to penetrate the skull, its effect on the rest of the brain is indiscriminate. It cannot be localized to change activity in certain parts of the brain without affecting others.

Abrams also argues that transcranial magnetic stimulation (TMS) is both a less dangerous and more controlled way of stimulating the brain. U.S. Pat. No. 4,940,453, to Cadwell, describes the type of magnetic coil used in TMS. The ability to produce a localized magnetic field, which in turn triggers localized electrical activity in the brain, has enabled TMS to be successful in the treatment of depression. Reduced activity in the left prefrontal cortex has been implicated in depression, and TMS may work by restoring activity in this area to normal levels. One problem with TMS is that high frequency stimulation may induce seizures. U.S. Pat. No. 5,769,778 describes a method of monitoring the EEG signal in order to prevent such seizures. When incipient features of a seizure are detected, the treatment is halted. Thus, the '778 patent describes a kind of limited feedback system, albeit one for preventing the adverse effects of TMS treatment, rather than one that attempts to improve the delivery of such.

Even though the aforementioned techniques have allowed some degree of alteration of brain signals incorporating the EEG signal as an indicator, there still exists a need for a system with a continuous feedback mechanism for monitoring and altering brain signals to treat certain diseases and conditions.

BRIEF SUMMARY OF THE INVENTION

The present invention comprises a method and device for producing a desired brain state in an individual. In its most general form, the method of the present invention comprises measuring the activity of the brain, analyzing the measured activity by comparing it to a desired brain activity, and directing one or more magnets to produce magnetic fields which will close the gap between the actual and desired brain state.

In its most general form, the device of the present invention comprises means for measuring the activity of the brain, a computational system for analyzing the measured activity by comparing it to a desired brain activity, and means for directing one or more magnets to produce magnetic fields which will close the gap between the actual and desired brain state.

In one embodiment of the invention, brain activity is revealed by the EEG signal, as measured with multiple electrodes on the surface of the skull. In another embodiment, brain activity is measured with magnetoencephalography (MEG), which is able to detect the weak magnetic fields emanating from the brain. In yet another embodiment, brain activity is measured by functional magnetic resonance imaging (fMRI), which measures blood flow in the brain and from which activity may be inferred.

In one embodiment, the computational system determines the single parameter (the parameters comprise spatial position, pulse strength, pulse frequency, and pulse duration for each magnet) controlling the magnets that most reduces the gap between the actual and desired brain state and alters this parameter accordingly. In another embodiment of the computational system, multiple parameters are altered simultaneously to reduce the gap between the actual and the desired brain states more efficiently. In another embodiment of the computational system, a subset of parameters are chosen for consideration based on a priori knowledge or based on experimentation. In yet another embodiment of the computational system, the mean magnitude of the changes to the parameters is reduced with time so that an approximate solution may be found first and fine tuned later. In a further computational embodiment, a random jump in the values of the parameters is effected if the current set of values is not yielding good results.

In one embodiment of the present invention, multiple magnets are used to produce magnetic fields to stimulate the brain and, optionally, each magnet may be positioned independently on the surface of the skull.

In an embodiment of the present invention, the device comprises electrodes for measuring the EEG signal; an amplifier for amplifying the EEG signal; a converter for converting the measured analog EEG signal into a digital signal; magnets for applying the magnetic field to the brain of the individual; and a positioning apparatus for controlling the position of the magnets on the skull of the individual.

In a further embodiment of the present invention, two magnets are used to treat depression, one exciting the left prefrontal cortex, and one inhibiting the right prefrontal cortex.

In another embodiment of the present invention, multiple magnets are used to induce relaxation by increasing the magnitude of the alpha rhythm and by increasing synchronization between the left and right hemispheres.

In the most general embodiment of the system, an arbitrary psychological state with a known correlated activity state as revealed by EEG, magnetoencephalography (MEG), or functional MRI may be achievable.

It is to be understood that both the foregoing general description and the following detailed description are exemplary, but are not restrictive, of the invention.

BRIEF DESCRIPTION OF THE DRAWINGS

The present invention is best understood from the following detailed description when read in connection with the accompanying drawings. It is emphasized that, according to common practice, the various features of the drawings are not to scale, rather, the dimensions of the various features are arbitrarily expanded or reduced for clarity. Included in the drawings are the following figures.

DETAILED DESCRIPTION OF THE INVENTION

The present invention comprises a method and device (system) for altering brain states of individuals by continuously monitoring EEG signals simultaneous with magnetic treatment in order to improve the efficacy of the treatment in a "closed loop feedback" system. A feedback system is necessary because it is problematic, if not impossible, to provide an explicit solution to the problem of predicting the effect of multiple magnetic pulsed signals on the brain. The three primary reasons supporting this are:

(1) the circuitry of the brain is not completely mapped and, thus, even if the original locus of stimulation on the surface of the cortex is known, it cannot always be predicted which areas of the brain will be affected by the spread of neural activation;

(2) the dynamics of the brain are not fully understood and, thus, even with a full connectivity map of the brain, it is still not possible to predict activation as a function of time; and (3) even if the problems discussed for (1) and (2) are solved, there will still be variations in the organization of the brain among individuals stemming from innate, neuroanatomical differences and differences in experience affecting synaptic efficacy, neither of which, in general, will be known prior to actual treatment.

Thus, there exists the need for an alternative mechanism to explicitly predicting and calculating the effect on the brain of changes in the applied magnetic field in order to provide an optimal magnetic signal to the brain in view of the desired treatment aimed at altering the brain state.

Figure 1:
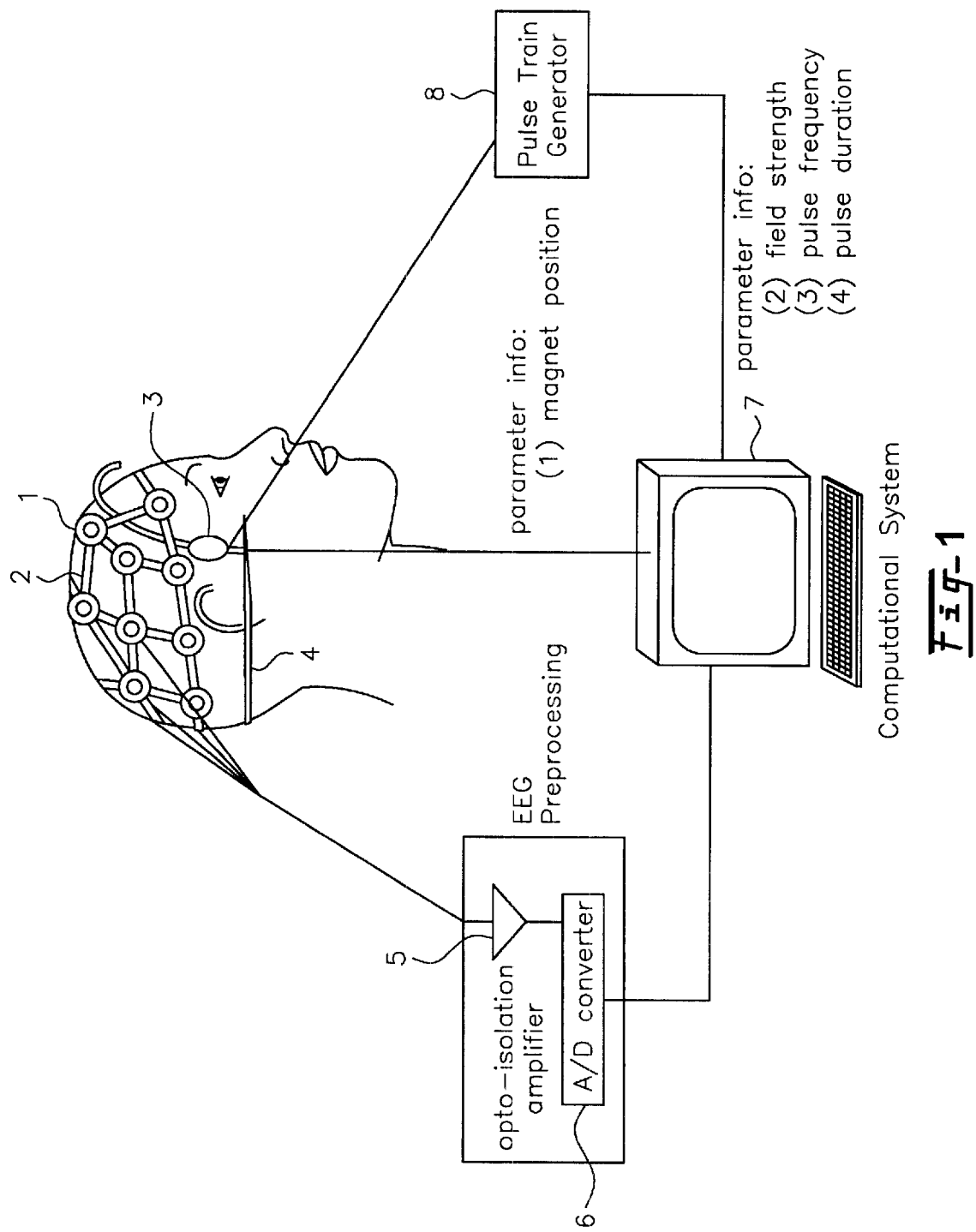
FIG. 1 shows the mechanism of the method and device of the present invention.

FIG. 1 shows an overview of the mechanism of the method and device used for adjusting the magnetic field delivered to the brain on the basis of EEG signals. There are five sets of components in the method and device: (1) those used in the direct monitoring of the EEG (or other type of) signal; (2) those that preprocess this signal for further computational processing; (3) those that process the EEG signals and determine the variation in the appropriate parameters for the magnetic field; (4) those producing the appropriate current for the magnetic field on the basis of these parameters; and (5) those responsible for delivering the magnetic field, itself, to the individual.

A set of electrodes 1 is placed in strategic positions on the surface of the skull as a means for measuring the EEG signal of an individual. The electrodes 1 may be placed individually on the skull, or may be held in place by a positioning apparatus, such as a lattice 2, as shown in FIG. 1. The lattice 2, in conjunction with a chin strap (not shown), holds the electrodes tightly against the skull, reducing impedance between the electrodes and the skull, thus improving the signal-to-noise ratio. Caps with pre-placed electrodes, which fit tightly over the head, can also be used to hold the electrodes on the skull. For purposes of the present invention, any structure which holds the electrodes tightly against the skull and does not interfere with the EEG signal can be used.

EEG wires connect each electrode 1 to a multi-channel opto-isolation amplifier 5. The amplifier 5 increases the relatively weak EEG signal received from the electrodes 1 and the amplified signal is then converted to a digital signal by a multi-channel analog to digital converter 6 for further processing by QEEG techniques. The amplifier 5 also optically isolates the electrodes from the rest of the system in order to prevent current from being accidentally shunted to them. Typically, the EEG signal will be monitored a short time after the magnetic field is generated, so that the EEG signal is not affected by the magnetic field created by the magnets. It may also be necessary in certain treatment regimes to allow the initial wave of activity to die down for a period of about 5 to 20 seconds before monitoring, to ensure that the field is generating more than a very short-term effect.

Although EEG is currently the most cost-effective means of monitoring the dynamic state of the brain for a given space and time resolution, other means are possible which do not in principle alter the nature of the proposed invention. Magnetoencephalography (MEG) directly detects the extremely weak magnetic fields produced by the brain with the use of one or more Superconducting Quantum Interference Devices (SQUIDS), as described in U.S. Pat. No. 4,700,135. It provides time resolution of approximately 1 millisecond, comparable to EEG, and spatial resolution of approximately 10 cm, also comparable to EEG. In addition, MEG does not suffer from some of the distortion effects due to the skull to which EEG signals are subject. However, MEG devices are considerably more expensive than EEG systems due to the need to keep the SQUIDS at a temperature near absolute zero, typically costing on the order of millions of dollars. Thus, the widespread use of MEG awaits a less costly apparatus.

Functional magnetic resonance imaging (fMRI) is another possible approach in acquiring a snapshot of brain activity (see U.S. Pat. No. 5,732,702). fMRI works by detecting differential blood flow to various regions of the brain, and from the blood flow levels, it infers brain activity. It uses a more powerful magnet than conventional MRI and it provides excellent spatial resolution (approximately 1 millimeter) with worse temporal resolution (on the order of seconds) than either EEG or MEG. Thus, to use it in a continuous feedback system, the parameters of the magnetic stimulation must be reduced by a priori means, effectively limiting the amount of time needed to search for the settings of the magnets that will provide optimal response. The temporal resolution of fMRI is improving with time, which will make it more amenable to monitoring tasks.

Figure 2:
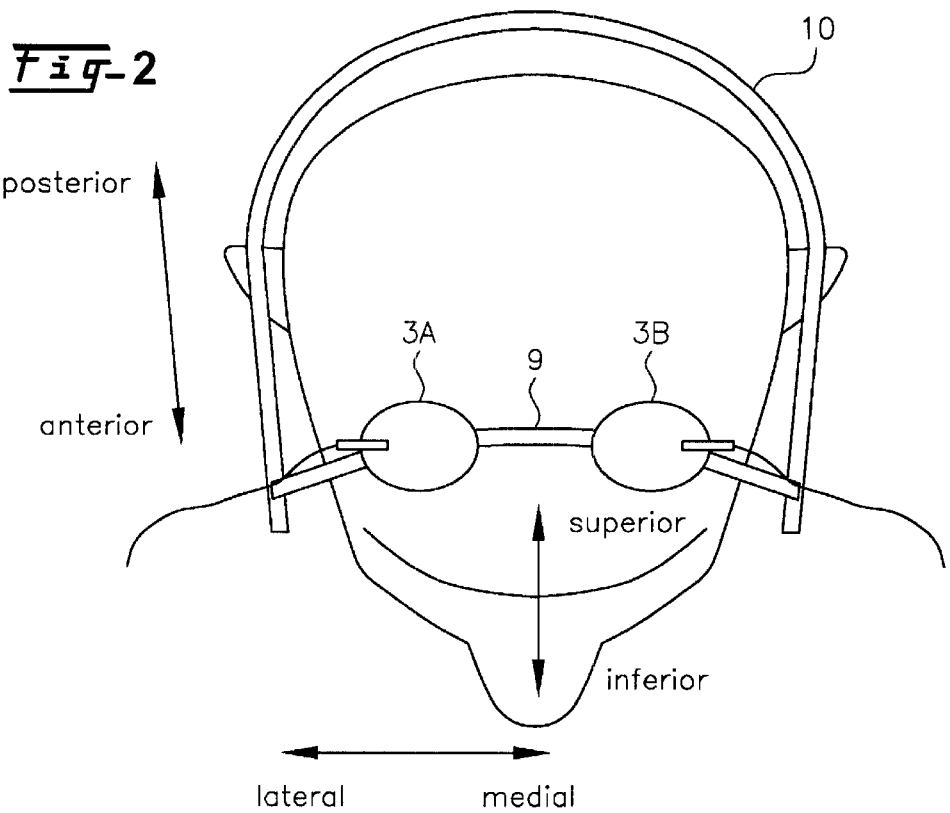
FIG. 2 is a top view of the magnet positioning system used in the method and device of the present invention.

The brain state, however it is measured, is funneled to a computation system 7 (FIG. 2), which lies at the heart of the feedback process. The system 7 compares the characteristics of the actual brain state to those of the desired brain state. The characteristics of the brain state are the temporal and spatial distributions of the various frequency bands of the brain signal, detectable by EEG or other methods and as described above, e.g., the mean frequency corresponding to various magnitudes of alpha, beta, delta, and theta rhythms. The therapeutic goal determines the gap between the measured and desired brain state, how the system 7 adjusts key parameters of the magnetic stimulation in order to reduce the gap between the actual and desired state, and what constitutes an acceptable brain state. For example, an acceptable brain state may be achieved by obtaining lower frequency states, between 1.5 and 7.5 Hz, to induce and/or maintain sleep, producing alpha frequency brain waves (between 8 and 13 Hz) to achieve calm or relaxation, etc. The algorithm for this adjustment process is described further below. The significant parameters which are altered are as follows:

(1) Magnet position—each magnet 3 may be moved to its optimal position by the magnet positioning apparatus 4, the mechanism of which is shown in FIG. 2.

(2) Magnitude of the magnetic field—each magnet will generate a unique field, a key component of which is the field strength. Greater magnitude implies more influence on the intended focus, although the size of that focus will also increase as the magnitude increases.

(3) Pulse frequency—each magnet will pulse at a unique frequency. Because the induced voltage in the brain is proportional to the change in the magnetic field strength, the effect on the brain is proportional to the pulse frequency. More specifically, frequencies below approximately 1 Hz suppress activity in the cortex, while frequencies above 1 Hz produce excitation in proportion to the frequency after an initial period of suppression. Thus, the focal area of the brain can be suppressed or excited depending on the magnet frequency.

(4) Pulse train duration—the object of most treatments will be to effect long-term synaptic change in the brain. The longer the train duration, the more likely that this will occur, although very long durations may be counterproductive, in that they can produce seizure-like conditions or other unknown side effects. Typical pulse train durations are in the range of 5 to 25 seconds.

The computational system 7 sends the determined parameters (2)–(4) to the pulse train generator 8, which, in turn, directs the magnets, i.e., means for applying a magnetic field, to produce the field as required by these parameter settings. The computational system 7 also sends the parameter values (1) directly to the positioning apparatus 4 which positions the magnets in the desired positions above the skull. FIG. 2 shows a system with two magnets, 3A and 3B, positioned above opposite cortical hemispheres, although not necessarily symmetrically. They are held in place by a circular bar 9 along which each magnet may be moved by a small motor from a lateral, anterior position along the side of the skull to a superior medial position above the skull midline. The bar 9 should be positioned such that the magnets 3A and 3B are as close as possible to the skull without touching the electrode mesh 2. The bar 9 contains a track 10 on which the bar 9 moves as a whole, also via a small motor, along with the magnets 3A and 3B. This mechanism allows positioning of the magnets 3A and 3B along the anterior/posterior dimension, i.e., from the front to the back of the skull. Thus, a magnet's movement over a combination of the bar 9 and the track 10 allow an arbitrary position to be achieved for the magnet in that magnet's hemisphere.

More bars 9 may be added if more magnets are needed in order to generate the requisite magnetic field characteristics. The entire positioning apparatus is suspended from above and may be lowered onto the head before the treatment session takes place. Ideally, the two bars 9 and 10 should also be adjustable to ensure that the magnets are close to the skull.

The chosen values for non-positional parameters for each magnet, i.e., the magnitude of the magnetic field, the pulse frequency, and the pulse train duration, are decided by and relayed from the computational system 7 to the pulse train generator 8, which, in turn, directs the magnets 3 to produce the calculated field. The non-positional (2)–(4) and the positional parameters (1) are set so as to minimize the distance between the desired EEG signal and the actual EEG signal. The following algorithm attempts to achieve this, assuming that a distance metric between the two EEG signals has been defined:

(1) an initial set of parameter values is chosen based on prior knowledge;

(2) for each parameter $P_i$ of n parameters the 2n Δ's resulting from increasing $P_i$ a fixed amount and decreasing $P_i$ a fixed amount are measured;

(3) the Δ among the 2n Δ's with the least value is determined;

(4) the corresponding parameter is adjusted in this direction; and (5) steps (1)–(4) are repeated until Δ is below a predetermined threshold.

Figure 3:
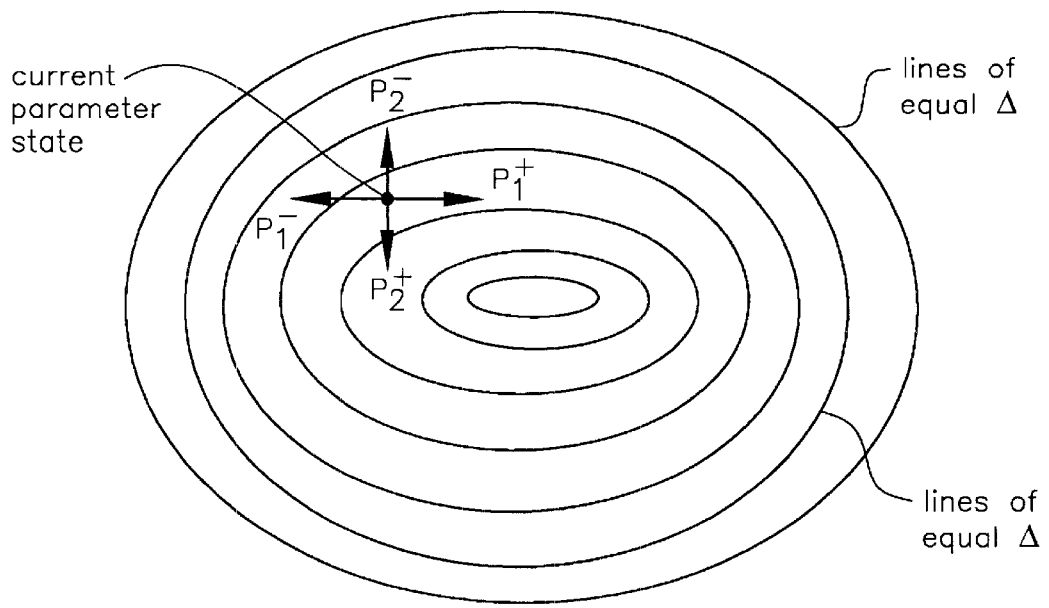
FIG. 3 shows the mechanism of gradient descent used for altering parameters of the magnetic field in the method of the present invention.

FIG. 3 illustrates the parameter adjustment process with n=2. The concentric ovals are lines of equal Δ as a function of the 2 parameters, $P_1$ and $P_2$, with the center oval the lowest. Among the four possible movements from the set of current parameter values ((1) increasing $P_1$, (2) decreasing $P_1$, (3) increasing $P_2$, and (4) decreasing $P_2$), increasing $P_2$ results in the lowest Δ. Thus, parameter $P_2$ is increased and, assuming that the cortical dynamics are relatively constant, the new EEG state resulting from this parameter change will be closer to the desired state. It can also be seen in FIG. 3 that the next change that will reduce Δ the most will be to increase $P_1$. The process continues until Δ is sufficiently small, i.e., something close to the desired EEG is being produced.

A number of variations of the basic algorithm may improve real-time performance, including:

(1) More than one parameter may be altered at once, in proportion to the decrease in Δ effected. Thus, in FIG. 3, $P_2$ would be increased and $P_1$ would be increased to a lesser extent. However, because the shape of the parameter space is not known in advance, it is uncertain at the outset whether this will improve performance. Empirical results will reveal if altering more than one parameter is useful for a given type of treatment.

(2) A subset of the parameters may be chosen, i.e., preselected, for modification such that the size of the search space is reduced. There may be too many parameters to alter in a timely manner (e.g., in the embodiment in FIG. 2, there are a total of eight parameters—movement, frequency, magnitude, and duration for each of the two magnets). The critical parameters may be chosen based on a priori knowledge or on the basis of experimentation.

(3) Parameter adjustment distance is decreased over time. This annealing process will ensure that larger changes occur at the start when the gradient is steepest and those changes will decrease toward the end when the gradient is much reduced.

(4) It may be necessary to induce a jump, or shift, in the parameter space if the minimization process does not produce an adequate result, i.e., no desired threshold is achieved. Such a jump or shift is effected by altering any or all of the parameters a random amount. The random amount may be determined by any computer program or other means for generating random numbers. This will be necessary, for example, if the system is stuck in a local minimum which is not adequate for the given treatment.

An example of the method and device of the present invention in operation is the treatment of depression. Currently, there are two TMS-based methods to redress the deficit in the cortical activity of the left prefrontal cortex relative to the right cortex. The first and most frequently used method is to apply rapid stimulation (greater than 1 Hz), to the left prefrontal cortex directly. The second method is to inhibit activity in the right cortex with low frequency stimulation. Both have proved effective (Menkes, et. al., 1999), however, neither method has shown success in greater than 50% of cases.

FIG. 2 shows the method and device with the current invention to increase treatment efficacy over the case in which only one hemisphere at a time is stimulated. One magnet would be centered over the left prefrontal cortex, while the other magnet would be centered over the right prefrontal cortex. The initial setting of the parameters would be approximately 5 Hz (high frequency) for the left magnet and 0.5 Hz (low frequency) for the right magnet. Magnitude levels would be set to be equivalent for both magnets. The desired EEG state is symmetry in the magnitude between the readings of the electrodes centered over the left and right prefrontal cortices, possibly with an additional preference given to signals that show coherence (waves with the same frequency and in phase) in these readings. The EEG signal is measured about 5 to 20 seconds after magnetic stimulation, after the initial wave of activation has died down, in order to ensure that the stimulation effected medium term and/or long term synaptic change; the feedback system of the present invention will adjust the position and frequency until there is firm evidence of an increase in bilateral symmetry.

As another example of the method of the present invention, it is known that the production of alpha waves (8–13 Hz) is correlated with a state of calm or relaxation. In addition, there is evidence that synchronization in this band between various parts of the brain, as revealed by the correlation between the EEG signals taken from those regions, is also associated with such a state. Using the prior technology, most likely with a larger magnet set in order to achieve large-scale synchronization, it should be possible to help invoke the alpha state regardless of the initial state of the brain. Furthermore, the method can be used to "lock-in" this state, prolonging the relaxation session. This is necessary because a sufficiently strong distracter, whether internal to the brain or from an external source, can cause the EEG signal to become desynchronized and to move to a higher frequency, interrupting relaxation and causing the mind to move to a state of alert readiness. The method of the present invention will prevent this interruption because, as soon as the EEG signal begins to become desynchronized, the device will immediately reapply the magnetic field originally found to induce the relaxed state (which will vary from patient to patient), or, if this fails, can reapply the feedback methodology to return to the desired state, returning the subject to the relaxed state.

Other variations of this method are also possible, such as producing and sustaining lower frequency states (1.5–7.5 Hz) as a means of inducing and maintaining sleep. In principle, an arbitrary EEG state can be achieved, as long as there exists a configuration and parameter setting of the current magnet set that can produce such an EEG signal.

Although illustrated and described above with reference to certain specific embodiments, the present invention is nevertheless not intended to be limited to the details shown. Rather, the present invention is directed to a continuous feedback method and device for altering brain states, and various modifications may be made in the details within the scope and range of equivalents of the claims and without departing from the spirit of the invention.

What is claimed:

1. A method for producing a desired brain state in an individual by measuring and controlling a brain signal comprising;
    measuring a brain signal indicating a brain state of an individual;
    comparing characteristics of the measured brain state to characteristics of a desired brain state to determine the difference between the measured brain state and the desired brain state;
    selecting a magnetic field having at least one parameter selected from the group consisting of magnet position, field magnitude, pulse frequency, and pulse train duration to alter the brain state, wherein the at least one parameter is selected to most reduce the gap between the measured and desired brain states;
    applying the selected magnetic field to the brain of the individual;
    measuring a brain signal indicating the altered brain state, the altered brain state corresponding to the application of the magnetic field;
    comparing the characteristics of the altered brain state to characteristics of the desired brain state to determine the difference between the altered brain state and the desired brain state; and
    repeating the selecting, applying, and measuring a brain signal indicating the altered brain state steps until an acceptable brain state is achieved.

2. The method of claim 1 wherein the steps are under computer control and the steps are performed continuously.

3. The method of claim 1 wherein the brain signal is measured by a technique selected from the group consisting of an electroencephalography, magnetoencephalography, and functional magnetic resonance imaging.

4. The method of claim 1 wherein the brain signal is an electroencephalogram signal measured by electrodes positioned on the head of the individual and the magnetic field is generated by magnets positioned on the head of the individual.

5. The method of claim 4 wherein the electroencephalogram signal is amplified and converted into a digital signal.

6. The method of claim 5 wherein at least one parameter is varied to alter the brain state.

7. The method of claim 6 wherein a gradient descent algorithm varies the parameters by:
    altering a preselected subset of the parameters selected of the group consisting of magnet position, field magnitude, pulse frequency, and pulse train duration;
    measuring distance metrices between a desired electroencephalogram signal and each electroencephalogram signal resulting from the alteration of each parameter of the subset of parameters;
    choosing the parameter and the parameter alteration having the distance metric with the least value;
    adjusting the chosen parameter by the chosen parameter alteration;
    measuring a resulting electroencephalogram signal, the resulting electroencephalogram signal corresponding to the chosen parameter alteration, and a resulting distance metric between the desired electroencephalogram signal and the resulting electroencephalogram signal; and
    repeating the adjusting and measuring a resulting electroencephalogram signal steps until a desired threshold is achieved.

8. The method of claim 6 wherein a gradient descent algorithm varies the parameters by:
    altering a preselected subset of the parameters by alteration distances, the parameters being selected from the group consisting of magnet position, field magnitude, pulse frequency, and pulse train duration, wherein more than one parameter is altered at a time,
    measuring distance metrices between a desired electroencephalogram signal and each electroencephalogram signal resulting from the alteration of each parameter of the subset of parameters;
    realtering the preselected subset of parameters, the parameter realteration distances being decreased from the alteration step, more Man one parameter being realtered at a time; and
    measuring a resulting electroencephalogram signal, the resulting electroencephalogram signal corresponding to the chosen parameter realteration, and a resulting distance metric between the desired electroencephalogram signal and the resulting electroencephalogram signal,
    wherein if a desired threshold is not achieved, each parameter of the subset of parameters is realtered a random amount to shift the parameter space and the altering, realteing, and measuring steps are repeated until a desired threshold is achieved.

9. The method of claim 5 wherein at least one parameter is increased and decreased by a fixed amount and the resulting brain state is measured.

10. The method of claim 9 wherein a gradient descent algorithm varies the parameters by:
    measuring distance metrices between a desired electroencephalogram signal and each electroencephalogram signal resulting from the increase and decrease of each parameter;
    choosing the parameter and the parameter increase or decrease having the distance metric with the least value;

adjusting the chosen parameter by the chosen parameter increase or decrease;

measuring a resulting electroencephalogram signal, the resulting electroencephalogram signal corresponding to the chosen parameter increase or decrease, and a resulting distance metric between the desired electroencephalogram signal and the resulting electroencephalogram signal; and repeating the adjusting and measuring a resulting electroencephalogram steps until a desired threshold is achieved.

11. The method of claim 9 wherein a gradient descent algorithm varies the parameters by:

measuring distance metrices between a desired electroencephalogram signal and each electroencephalogram signal resulting from the increase and decrease of each parameter, choosing for each parameter the parameter increase or decrease having the distance metric with the least value;

adjusting more than one parameter by the chosen parameter increase or decrease having the distance metric with the least value, each parameter being increased or decreased an amount inversely proportional to the measured distance metric for each increase or decrease;

measuring a resulting electroencephalogram signal, the resulting electroencephalogram signal corresponding to the chosen parameter increase or decrease, and a resulting distance metric between the desired electroencephalogram signal and the resulting electroencephalogram signal; and repeating the adjusting and measuring a resulting electroencephalogram signal steps until a desired threshold is achieved.

12. The method of claim 9 wherein a gradient descent algorithm varies the parameters by:

measuring distance metrices between a desired electroencephalogram signal and each electroencephalogram signal resulting from the increase and decrease of each parameter;

choosing the parameter and the parameter increase or decrease having the distance metric with the least value;

adjusting the chosen parameter by the chosen parameter increase or decrease;

measuring a resulting electroencephalogram signal, the resulting electroencephalogram signal corresponding to the chosen parameter increase or decrease, and a resulting distance metric between the desired electroencephalogram signal and the resulting electroencephalogram signal; and repeating the adjusting and measuring a resulting electroencephalogram steps until a desired threshold is achieved, wherein the adjustment of the chosen parameter decreases for each repeated adjustment step.

13. The method of claim 9 wherein a gradient descent algorithm varies the parameters by:

measuring distance metrices between a desired electroencephalogram signal and each electroencephalogram signal resulting from the increase and decrease of each parameter;

choosing the parameter and the parameter increase or decrease having the distance metric with the least value;

adjusting the chosen parameter by the chosen parameter increase or decrease; and measuring the resulting electroencephalogram signal, the resulting electroencephalogram signal corresponding to the chosen parameter increase or decrease, and a resulting distance metric between the desired electroencephalogram signal and the resulting electroencephalogram signal, wherein if a desired threshold is not achieved, each parameter is altered a random amount to shift the parameter space and the increasing, decreasing, first and second measuring, choosing, and adjusting steps are repeated until a desired threshold is achieved.

14. The method of claim 1 wherein the magnets are positioned using a bar holding the magnets, the bar being movable along a track by a motor.

15. The method of claim 1 wherein the brain signal is altered to correct asymmetry in the brain signal between the left and right hemispheres associated with clinical depression.

16. The method of claim 1 wherein alpha rhythms of the brain state are altered to produce a greater degree of relaxation.

17. The method of claim 1 wherein the brain signal is altered to achieve an arbitrary electroencephalogram signal corresponding to a desired brain state.

18. The method of claim 1 wherein the parameters are selected based on known brain signals corresponding to brain states.

19. The method of claim 18 wherein the brain states are selected from the group consisting of lower frequency states, alpha frequency states, frequencies suppressing activity in the cortex, and frequencies producing excitation of the cortex.

20. The method of claim 1 wherein the parameters of the magnetic field are selected based on treatment regimes for known conditions.

21. A method for producing a desired brain state in an individual by continuously measuring and controlling a brain signal comprising:

measuring an electroencephalogram signal indicating a brain state of an individual by electrodes positioned on the head of the individual;

amplifying the measured electroencephalogram signal;

converting the amplified electroencephalogram signal into a digital signal;

comparing the characteristics of the digital electroencephalogram signal to the characteristics of a desired electroencephalogram signal using a computational system to determine the difference between the digital electroencephalogram signal and the desired electroencephalogram signal;

applying a magnetic field having parameters, the parameters being magnet position, field magnitude, pulse frequency, and pulse train duration, to alter the brain state of the individual by positioning magnets on the head of the individual, wherein a value for at least one parameter is selected to alter the brain state and achieve the desired electroencephalogram signal;

measuring a resulting electroencephalogram signal, the resulting electroencephalogram signal corresponding to the selected value of the at least one parameter; and comparing the characteristics of the resulting electroencephalogram signal to the characteristics of the desired electroencephalogram signal to determine the need to further alter the brain state, wherein the steps are under computer control, the method is continuous, and the at least one parameter is varied according to a gradient descent algorithm.

22. A device for producing a desired brain state in an individual by measuring and controlling a brain signal comprising;
    means for measuring a brain signal indicating a brain state of an individual;
    a computational system for comparing characteristics of the measured brain state to characteristics of a desired brain state to determine the difference between the measured brain state and the desired brain state; and
    means for applying a magnetic field having parameters to the brain of the individual to alter the brain state, the parameters being magnet position, field magnitude, pulse frequency, and pulse train duration.

23. The device of claim 22 wherein the means for applying a magnetic field are magnets.

24. The device of claim 23 wherein the means for measuring the brain signal is selected from the group consisting of an electroencephalogram, a magnetoencephalogram, and a functional magnetic resonance imager.

25. The device of claim 24 wherein the brain signal is measured by an electroencephalogram using electrodes positioned on the head of the individual.

26. The device of claim 25 further comprising an amplifier for amplifying the electroencephalogram signal.

27. The device of claim 26 further comprising an analog/digital converter to convert the amplified electroencephalogram signal into a digital signal.

28. The device of claim 23 further comprising a positioning apparatus for controlling the position of the magnets on the skull of the individual, the positioning apparatus using a bar holding the magnets, the bar being movable along a track by a motor.

29. The device of claim 28 wherein the positioning apparatus enables movement of the magnets between the front and back of a skull.

30. A device for producing a desired brain state in an individual by measuring and controlling an electroencephalogram signal comprising:
    electrodes for measuring the electroencephalogram signal of an individual, the electrodes being adapted to be positioned on the surface of the skull and having wires for relaying the electroencephalogram signal;
    a lattice for holding the electrodes on the surface of the skull;
    a multi-channel opto-isolation amplifier for receiving the electroencephalogram signal from the wires of the electrodes and amplifying the electroencephalogram signal relayed by the electrodes;
    an analog/digital converter for converting the measured signal into a digital signal;
    a computational system including quantitative electroencephalogram software for monitoring the electroencephalogram signal and comparing the signal to a desired electroencephalogram signal to determine the difference between the measured electroencephalogram signal and the desired electroencephalogram signal;
    a pulse train generator for generating a magnetic field having a field magnitude, a pulse frequency, and a pulse train duration in accordance with the determination of the computational system;
    magnets to apply the magnetic field to the brain of the individual to alter the brain state; and
    a positioning apparatus for controlling the position of the magnets on the skull of the individual in accordance with the determination of the computational system, the positioning apparatus using a bar holding the magnets, the bar being moveable along a track by a motor, and the positioning apparatus enabling movement of the magnets between the front and back of the skull.

* * * * *